United States Patent

Shvo

Patent Number: 5,618,942
Date of Patent: Apr. 8, 1997

[54] PRODUCTION OF 2,3,5,6-TETRACHLOROPYRIDINE

[75] Inventor: Youval Shvo, Kfar Shemaryahu, Israel

[73] Assignee: Luxembourg Industries (Pamol) Ltd., Tel-Aviv, Israel

[21] Appl. No.: 602,806

[22] PCT Filed: Sep. 2, 1994

[86] PCT No.: PCT/US94/10010

§ 371 Date: Mar. 15, 1996

§ 102(e) Date: Mar. 15, 1996

[87] PCT Pub. No.: WO95/06639

PCT Pub. Date: Mar. 9, 1995

[30] Foreign Application Priority Data

Sep. 3, 1993 [IL] Israel ................. 106901

[51] Int. Cl.$^6$ ............... C07D 213/46; C07D 213/53
[52] U.S. Cl. ............................................. 546/250
[58] Field of Search ................... 546/250, 345

[56] References Cited

U.S. PATENT DOCUMENTS

| | | | |
|---|---|---|---|
| 4,996,323 | 2/1991 | Pews | 546/250 |
| 5,017,705 | 5/1991 | Becker | 546/250 |
| 5,106,984 | 4/1992 | Halpern | 546/250 |
| 5,200,522 | 4/1993 | Grozinger | 546/250 |
| 5,206,372 | 4/1993 | Schrodier | 546/294 |
| 5,229,519 | 7/1993 | Zhang | 546/250 |
| 5,480,995 | 1/1996 | Kraus | 546/250 |
| 5,493,028 | 2/1996 | Zhang | 546/250 |
| 5,508,410 | 4/1996 | Murugan | 546/250 |

*Primary Examiner*—C. Warren Ivy
*Assistant Examiner*—D. Margaret M. Mach
*Attorney, Agent, or Firm*—Oliff & Berridge

[57] ABSTRACT

A novel, simple, high-yield process for the production of 2,3,5,6-tetrachloropyridine comprises reacting an ester of 2,2,4-trichloro-4-cyanobutyric acid with excess phosphorus oxychloride in the presence of a catalytic amount of hydrogen chloride and optionally in the presence of an aprotic inert solvent, at a temperature of 100°–160° C., preferably at 120°–140° C. for about 5–10 hours, under elevated pressure, if necessary.

14 Claims, No Drawings

PRODUCTION OF 2,3,5,6-TETRACHLOROPYRIDINE

This application is a 371 of PCT/US94/10010, filed Sep. 2, 1994 published as WO95/06639 on Mar. 9, 1995.

The present invention relates to a novel, improved process for the production of 2,3,5,6-tetrachloropyridine, also known as Symtet.

2,3,5,6-tetrachloropyridine is useful as an intermediate in the production of various herbicides, fungicides and insecticides, for example the important insecticide O,O-diethyl-O-3,5,6-trichloro-2-pyridyl phosphorothioate.

Various processes are -known for the production of 2,3,5,6tetrachloropyridine. For example, it can be prepared by the liquid phase chlorination of β-picoline (U.S. Pat. No. 4,483,993) or pyridine (U.S. Pat. No. 4,515,953) or by vapor phase chlorination of 2-chloropyridine or 2,6-dichloropyridine (U.S. Pat. No. 3,251,848).

Israel Patent 61581 describes a process whereby a mixture of 2,3,5,6-tetrachloropyridine and 3,5,6-trichloropyridin-2-ol is obtained by reacting trichloroacetyl chloride and acrylonitrile in a solvent at ca 170° C. using various metals as catalysts (yields were not reported).

European Patent Application 0 030 215 describes the preparation of 3,3,5-trichloroglutaric acid imide and its subsequent conversion with dehydrating agents such as POCl₃ to 2,3,5,6-tetrachloropyridine.

Unexpectedly, we have discovered that 2,2,4-trichloro-4cyanobutyrate esters, e.g. the ethyl ester, undergo a one-step conversion to 2,3,5,6-tetrachloropyridine as described in the following equation, where R is an alkyl, aralkyl or aryl group:

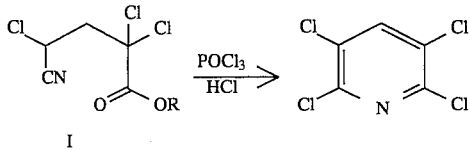

As used herein "aryl" means an aromatic hydrocarbon radical of $C_6$ to $C_{10}$ carbon atoms which may optionally be substituted with lower alkyl and/or halo. As used herein "aralkyl" means a $C_1$–$C_6$ alkyl group substituted with an aryl radical as defined above.

This novel and remarkably simple transformation results in yields of 60–90% of 2,3,5,6-tetrachloropyridine, depending on the chemical nature of R. The reaction is carried out using POCl₃, a readily available commercial material, at a temperature of 100° to 160° C., preferably at 120°–140° C., in the presence of a catalytic amount of hydrogen chloride. At this preferred temperature range, the reaction time is 5–10 hours. The molar ratio of POCl₃ to the 2,2,4-trichloro-4-cyanobutyrate ester is in the range of 10:1 to 1:1. The preferred range is 2:1 to 3:1. If a high ratio is used, it is recommended to distill out and recycle the excess POCl₃ at the end of the reaction. After the reaction is completed, excess POCl₃ is distilled off, water is added to the residue and the mixture is extracted with a suitable organic solvent, containing now crude 2,3,5,6-tetrachloropyridine. The pure product is isolated by conventional methods, such as sublimation, crystallization or steam distillation. The product thus obtained exhibited a m.p. 89°–90° C.; ¹H-NMR (CDCl₃): δ7.88 ppm (singlet), and was found to be identical in all respects with an authentic sample of 2,3,5,6-tetrachloropyridine.

Dry HCl gas in the amount of 0.5–5% by weight of the combined reactant and solvent is recommended. The preferred range is 1.5–3%. The reaction is autocatalytic in the sense that HCl is being produced as the reaction is progressing.

The reaction may also be carried out in the presence of an aprotic and non-reactive solvent, such as aromatic and aliphatic hydrocarbons as well as halogenated hydrocarbons, without seriously affecting the reaction efficiency.

The starting materials of formula I above, i.e. ethyl 2,2,4-trichloro-4-cyanobutyrate and other esters of 2,2,4-trichloro-4-cyanobutyric acid, can be readily prepared according to methods known in the art which are described in the chemical literature, for example: The Journal of Organic Chemistry, Vol. 29, pp. 2104–5 (1964); and Tetrahedron, Vol. 29, pp. 827–832 (1973); Journal of Organic Chemistry, Vol. 41, pp. 396–398 (1976); and U.S. Pat. No. 5,017,705.

The simplicity of the process described herein makes it amenable to large scale production. The high yields obtained with lower alkyl esters render the process attractive from the economical point of view. Although an excess of POCl₃ has to be used, 80% are recovered and can be recycled. The process is also ecologically sound, as the main by-products in the high yield reactions are phosphoric acid and its esters (the latter can be hydrolyzed to the former).

The invention will now be described in detail by means of the following non-limiting examples.

EXAMPLE 1

Ethyl 2,2,4-trichloro-4-cyanobutyrate (12.0 g) and phosphorus oxychloride (40 mL) and dry HCl gas (1.5 g) were placed in a sealed glass reactor that was immersed in a thermo-regulated oil bath at 140° C. After 10 hours at the above temperature, the reactor was cooled to ambient temperature and volatiles were distilled off at 106° C. to give 32 mL of POCl₃. Crushed ice was added to the distillation residue, the slurry was stirred for 15 minutes and then extracted with methylene chloride. The methylene chloride was distilled out and the residue was subjected to sublimation at 30°–35° C./0.2 mmHg. The collected white crystalline solid, 2,3,5,6-tetrachloropyridine, weighed 9.6 g (90.6% yield), m.p. 88°–90° C.

EXAMPLE 2

Example 1 was repeated as described above, but the duration of heating at 140° C. was reduced to 5 hours. The weight of 2,3,5,6tetrachloropyridine obtained after sublimation was 7.2 (68% yield).

EXAMPLE 3

Phenyl 2,2,4-trichloro-4-cyanobutyrate (12.0g), phosphorus oxychloride (40 mL) and dry HCl gas (1.4 g) were heated at 140° C. for 10 hours. The resulting reaction mixture was worked up as described in Example 1. A volume of 33 mL of POCl₃ was recovered. The sublimed product, 2,3,5,6-tetrachloropyridine, weighed 5.34 g (60% yield).

EXAMPLE 4

Example 3 was repeated as described above, but the reaction temperature was lowered to 110° C. and reaction time was reduced to 5 hours. The methylene chloride solution was evaporated, weighed and analyzed by GLC with an internal standard. The analysis indicated 62% yield of 2,3,5,6-tetrachloropyridine.

EXAMPLE 5

Butyl 2,2,4-trichloro-4-cyanobutyrate (12 g), phosphorus oxychloride (40 mL) and dry HCl gas (1.6 g) were heated at 140° C. for 10 hours. The resulting reaction mixture was worked up as described in Example 1 and 32 mL of POCl₃ were recovered. The methylene chloride solution obtained after work-up was analyzed by GLC with an internal standard. The analysis indicated a 62% yield of 2,3,5,6-tetrachloropyridine.

EXAMPLE 6 p-tolyl 2,2,4-trichloro-4-cyanobutyrate (12 g), phosphorus oxychloride (40 mL) and dry HCl gas (1.6 g) were heated at 140° C. for 10 hours. After cooling to ambient temperature, ice was added and the aqueous slurry was subjected to steam distillation. The white solid was filtered off from the water distillate and dried in vacuum at 60° C. to a constant weight. The dried solid, 2,3,5,6-tetrachloropyridine had a m.p. of 87°–88° C. and weighed 6.03 g (71% yield).

EXAMPLE 7

Methyl 4-cyano-2,2,4-trichlorobutyrate (12 g), phosphorus oxychloride (16.5 mL) and xylene (16 mL) were placed in a glass lined reactor which was pressurized with dry HCl to 4 atmospheres, and then heated for 10 hours at 140° C. The pressure increased gradually to 20 atmospheres. The resulting cooled reaction mixture was poured into cold water and subjected to steam distillation. The organic phase of the distillate was separated and assayed (HPLC) for 2,3 5,6-tetrachloropyridine, 9.4 g (83% yield).

EXAMPLE 8

Example 7 was repeated, substituting the volume of xylene by an identical volume of cyclohexane. The cooled reaction mixture was poured into cold water, the organic phase separated and the aqueous phase was extracted with 2×15 mL hot cyclohexane. The combined organic extract was washed with sodium carbonate solution, water and assayed (HPLC) for 2,3,5,6-tetrachloropyridine, 9.06 g (80% yield).

EXAMPLE 9

Example 8 was repeated, substituting the volume of cyclohexane by an identical volume of 1,2-dichloroethane. After treating the reaction mixture as described in Example 8, there was obtained 2,3,5,6-tetrachloropyridine, 8.8 g (78%).

EXAMPLE 10

A mixture of methyl 4-cyano-2,2,4-trichlorobutyrate (12 g), phosphorus oxvchloride (20 g) was treated as described in Example 7. After cooling to 70° C., the thick dark reaction mixture was poured into cold water. The resulting slurry was subjected to steam distillation to give white crystalline 2,3,5,6-tetrachloropyridine which, after drying, weighed 8.9 g (79% yield).

I claim:

1. A process for the production of 2,3,5,6-tetrachloropyridine which comprises reacting, at a temperature at least 100° C., an ester of 2,2,4-trichloro-4-cyanobutyric acid of the general formula I with POCl₃ in the presence of a catalytic amount of hydrogen chloride to produce compound II according to the following reaction:

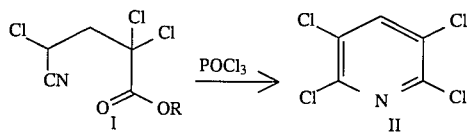

in which R is an alkyl, aryl or aralkyl group.

2. A process according to claim 1, wherein the hydrogen chloride comprises dry hydrogen chloride gas.

3. A process according to claim 1, wherein the ester is derived from a $C_1$–$C_6$ alkanol.

4. A process according to claim 1, wherein the ester comprises ethyl 2,2,4-trichloro-4-cyanobutyrate.

5. A process according to claim 1, wherein the ester comprises methyl 2,2,4-trichloro-4-cyanobutyrate.

6. A process according to claim 1, wherein the molar ratio of POCl₃ to the 2,2,4-trichloro-4-cyanobutyrate ester is at least 1.

7. A process according to claim 6, wherein the molar ratio of POCl₃ to the 2,2,4-trichloro-4-cyanobutyrate ester is in the range of 10:1 to 1:1.

8. A process according to claim 7, wherein said ratio is in the range of 2:1 to 3:1.

9. A process according to claim 1 carried out in the presence of an aprotic inert solvent.

10. A process according to claim 9, wherein the solvent is selected from aromatic or aliphatic hydrocarbons and halogenated hydrocarbons.

11. A process according to claim 1, wherein the reacting is performed at a temperature of 100°–160° C.

12. A process according to claim 1, wherein the reacting is performed at atmospheric pressure or a pressure above atmospheric pressure.

13. A process according to claim 12, wherein the pressure is greater than 1 and up to 20 atmospheres.

14. A process according to claim 1, wherein the reacting has a duration of about 5 to 10 hours.

* * * * *